United States Patent [19]

Yamamoto et al.

[11] Patent Number: 4,666,577

[45] Date of Patent: May 19, 1987

[54] METHOD OF RECORDING ELECTROPHORETIC IMAGE PATTERN

[75] Inventors: Hidehiko Yamamoto; Nobutaka Kaneko, both of Tokyo, Japan

[73] Assignee: Olympus Optical Co., Ltd., Tokyo, Japan

[21] Appl. No.: 826,991

[22] Filed: Feb. 7, 1986

[30] Foreign Application Priority Data

Feb. 7, 1985 [JP] Japan .................................. 60-22621
Feb. 7, 1985 [JP] Japan .................................. 60-22622
Feb. 9, 1985 [JP] Japan .................................. 60-22747

[51] Int. Cl.⁴ ..................... C25D 13/06; C25D 13/16; C25B 7/00
[52] U.S. Cl. .............................. 204/183.3; 204/180.1; 204/299 R; 204/300 R
[58] Field of Search ............. 204/180.1, 183.3, 299 R, 204/300 R

[56] References Cited

U.S. PATENT DOCUMENTS

| | | | |
|---|---|---|---|
| 3,869,365 | 3/1975 | Sunden | 204/183.3 |
| 3,912,609 | 10/1975 | Arlinger | 204/183.1 |
| 3,941,678 | 3/1976 | Akiyama | 204/183.3 |
| 4,154,669 | 5/1979 | Goetz | 204/180.1 |
| 4,181,594 | 1/1980 | Rizk et al. | 204/299 R |
| 4,315,812 | 2/1982 | Karlson | 204/183.3 |
| 4,416,762 | 11/1983 | Akiyama | 204/183.3 |
| 4,456,513 | 6/1984 | Kawai et al. | 204/183.3 |
| 4,569,739 | 11/1986 | Klinkowski | 204/180.1 |
| 4,594,064 | 6/1986 | Anderson | 204/299 R |

FOREIGN PATENT DOCUMENTS 3127007 3/1982 Fed. Rep. of Germany ... 204/180 R

Primary Examiner—Arthur P. Demers
Attorney, Agent, or Firm—Parkhurst & Oliff

[57] ABSTRACT

In a method of printing on a test report a pattern of fraction images of various kinds of proteins contained in a serum sample, an electrophoretic signal obtained by photoelectrically scanning a substrate bearing electrophoretic images is sampled to derive a number of digital samples, a reference digital sample having a maximum amplitude and denoting a peak point of albumin component is detected, a predetermined number of digital samples are extracted on the basis of the reference digital sample having the maximum amplitude, an electrophoretic image pattern is printed on a test report by using the extracted digital samples such that the reference digital sample is recorded at a predetermined point on the test report.

22 Claims, 14 Drawing Figures

FIG.4A _PRIOR ART_
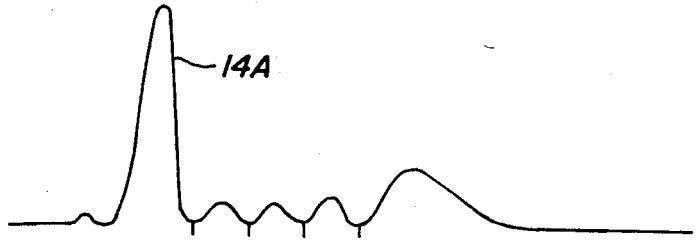
FIG.4B
_PRIOR ART_
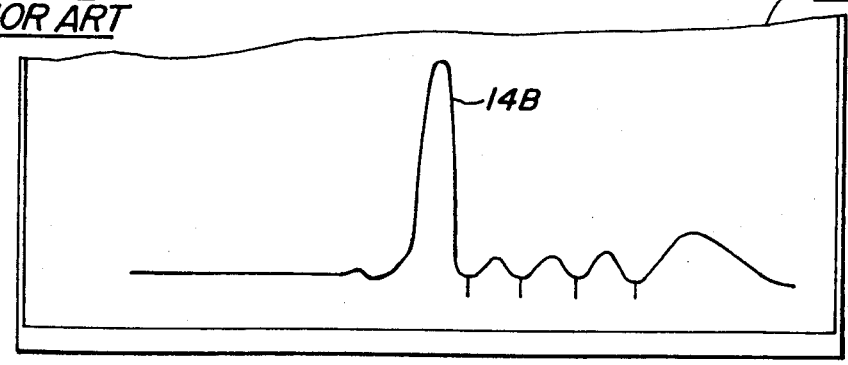

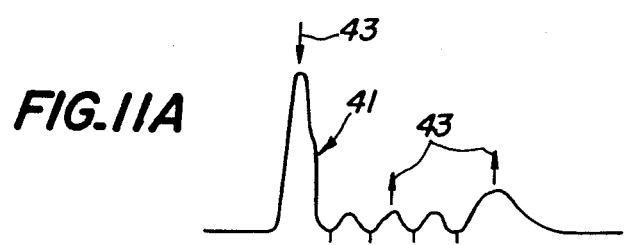
FIG_11A
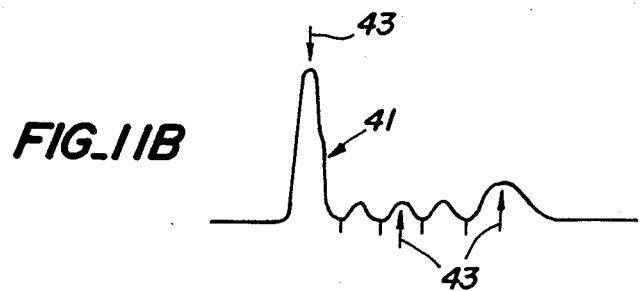
FIG_11B
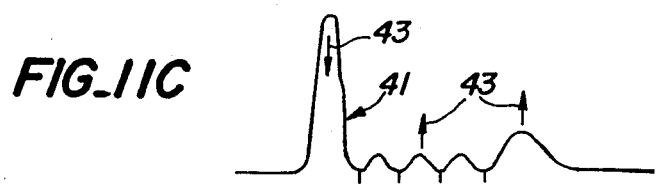
FIG_11C
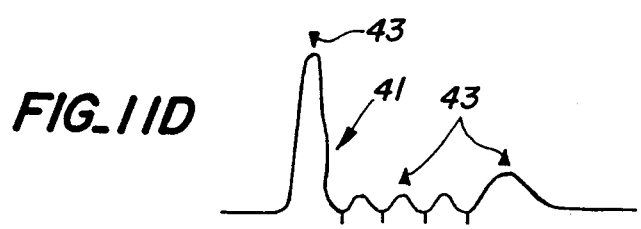
FIG_11D
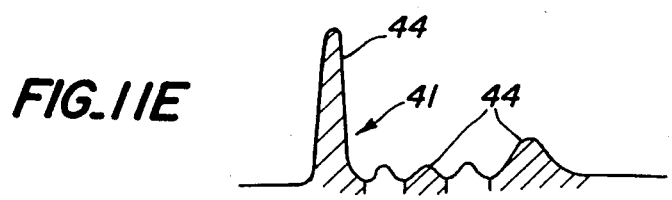
FIG_11E

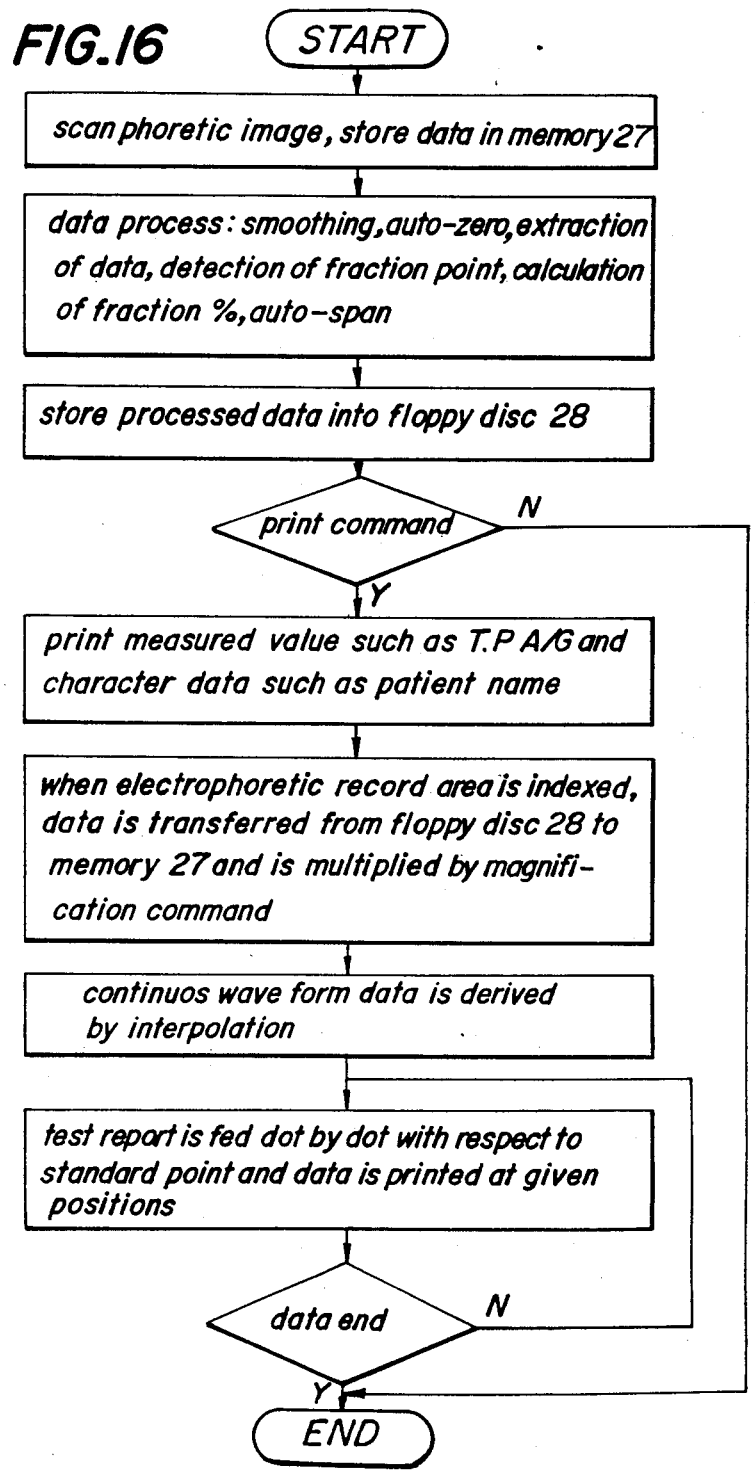

FIG_17A 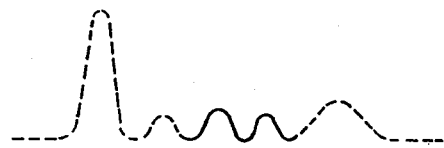
FIG_17B 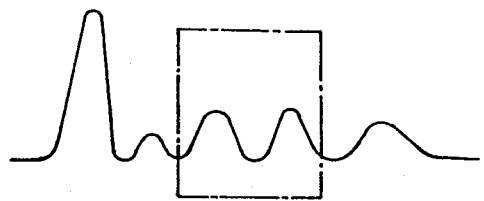
FIG_17C 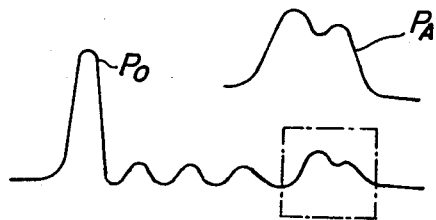

METHOD OF RECORDING ELECTROPHORETIC IMAGE PATTERN

BACKGROUND OF THE INVENTION

Field of the Invention and Related Art Statement

The present invention relates to a method of recording an electrophoretic image pattern of various components contained in a biological sample.

In an electrophoresis, a sample such as a serum is applied on a substrate such as a cellulose acetate film by mean of an applicator and is subjected to an electrophoresis in an electrophoretic vessel for a given time. Then the substrate is dyed, decolored and dried successively. Further the substrate is introduced in a densitometer containing a decalin and electrophoretic images are made visible. Then these images are photoelectrically scanned by a light beam.

FIG. 1 is a schematic view showing a principal construction of the densitometer of electrophoretic apparatus. A substrate 1 which has been previously dyed, decolored and dried is fed by feeding rollers 2 into a photometering section 4 containing decalin 3 for making the substrate 1 transparent. The substrate 1 is photometered by the photometer device 5 and then is discharged by means of discharge rollers 6. The photometer device 5 comprises a light source 5a for emitting a light beam and a light receiving element 5b for receiving a light beam transmitted through the substrate 1. The photometer device 5 is moved in a scanning direction b perpendicular to a feeding direction a of the substrate 1 as illustrated in FIG. 2. In this manner electrophoretic images 7 of various components formed on the substrate 1 is photoelectrically scanned to produce a photometered signal.

The photometered signal thus obtained by scanning the electrophoretic images 7 in the densitometer is sampled at a suitable sampling period to derive digital samples. Various measured values of test items e.g. fraction percentages are calculated from the samples thus obtained and these values are printed on a test report by a printer. On the test report, a pattern of the electrophoretic images 7 is also recorded. In case of a serum sample of a human being, an electrophoretic image pattern 14 shown in FIG. 3 is recorded on the test report, said pattern including fraction image 8 of pre-albumin, fraction image 9 of albumin (Alb), fraction image 10 of $\alpha_1$-globulin ($\alpha_1$-G), fraction image 11 of $\alpha_2$-globulin ($\alpha_2$-G), fraction image 12 of $\beta$-globulin ($\beta$-G) and fraction image 13 of $\gamma$-globulin ($\gamma$-G), these images being successively recorded in the order mentioned above.

In a known method of recording the electrophoretic image pattern 14 on the test report, a predetermined number of samples reckoned from a mechanical scan start point or a point separated from said start point by a predetermined distance are exclusively used to form the pattern 14. Therefore, when the substrate 1 is fed along an inclined path with respect to its longitudinal axis, an electrophoretic image pattern 14B printed on a test report 15B shown in FIG. 4B is shifted in position with respect to an electrohoretic image pattern 14A which is formed on a test report 15A illustrated in FIG. 4A when the substrate 1 is fed along a correct path parallel to its longitudinal axis. Then a necessary part of the pattern might not be printed on the test report. Further, the shift in position of the electrophoretic image patterns on the test reports might hazard the easy and accurate inspection of the electrophoretic image patterns printed on test reports.

In some electrophoretic apparatuses, the electrophoretic time may be varied in order to analyze various samples or to make the process speed adjustable. In such apparatus the sampling period is made longer or shorter when the electrophoretic time is longer or shorter, because a length over which the electrophoretic images are expanded is proportioned to the electrophoretic time. Samples thus obtained are processed in the usual manner, and the measured values and electrophoretic image pattern are printed on a test report card. However, in such apparatuses, since the scanning range and scanning speed in the densitometer are remained constant in regardless to the electrophoretic time, the number of samples obtained by a single scan is varied in accordance with the electrophoretic time. That is to say, the number of samples becomes larger when the electrophoretic time is shorter and the sampling period is shorter. Therefore, when the electrophoretic image pattern is printed on the test report by processing the samples in a usual manner, the electrophoretic image patterns recorded on the test reports are shifted from each other as illustrated in FIGS. 4A and 4B and, in the worst case necessary data might not be recorded.

SUMMARY OF THE INVENTION

The present invention has for its object to provide novel and useful method of recording electrophoretic image patterns in a stable and accurate manner even if substrates are fed in an inclined fashion in the densitometer of the electrophoretic apparatus or the electrophoretic time is varied.

According to the invention, a method of recording an electrophoretic image pattern of components contained in a sample on a test report comprises the steps of:

(a) processing an electrophoretic image signal obtained by photoelectrically scanning electrophoretic images formed on a substrate to detect a predetermined reference point in the electrophoretic images;

(b) extracting a given portion of the electrophoretic image signal on the basis of the detected reference point; and (c) recording an electrophoretic image pattern in accordance with the extracted portion of the electrophoretic image signal.

According to a preferred embodiment of the method of recording the electrophoretic image pattern according to the invention, the electrophoretic image signal is consisting of a number of samples which are obtained by sampling a photoelectric signal derived by photoelectrically scanning the electrophoretic images with a given sampling period, a sample which represents a feature of a predetermined fraction image, i.e. a center point of a fraction image of albumin is extracted by utilizing a known image processing method, a predetermined number of samples are extracted on the basis of said extracted sample, and finally the electrophoretic image pattern is recorded by using the extracted samples.

In another preferred embodiment of the method according to the invention, an electrophoretic expansion length over which the electrophoretic images are expanded is detected and said sampling period is determined in proportion to the detected electrophoretic expansion length.

According to further aspect of the invention, various measured values are calculated from the extracted samples and then are compared with normal ranges, and when a measured value of a certain component is out of a normal range, an abnormal mark is also printed on the test report at a fraction image of the corresponding fraction image. In a preferred embodiment, said abnormal mark has such a shape that the mark can indicate in which direction a measured value deviates with respect to the normal range.

According to still another aspect of the invention, at least a part of an electrophoretic image pattern is printed at any desired magnification or size.

BRIEF DESCRIPTION OF THE DRAWINGS

FIGS. 4A and 4B are plan views showing test reports on which electrophoretic image patterns are printed by the known method;

FIGS. 11A to 11E are schematic views showing various embodiments of abnormal mark;

FIG. 16 is a flow chart representing the operation of another embodiment of the recording method according to the invention; and FIGS. 17A to 17C show electrophoretic image patterns printed on test reports by the method according to the invention.

DESCRIPTION OF THE PREFERRED EMBODIMENTS

Figure 1:
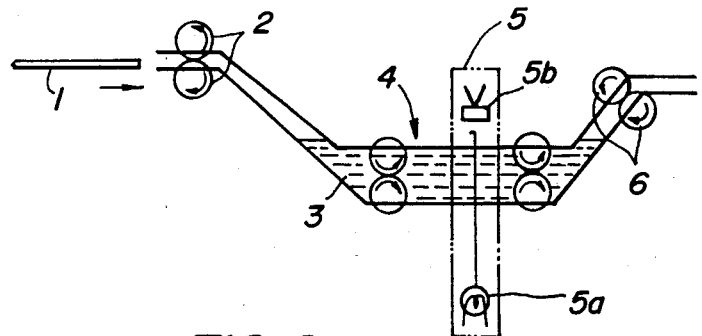
FIG. 1 is a schematic view showing a known densitometer for use in the electrophoresis.
Figure 2:
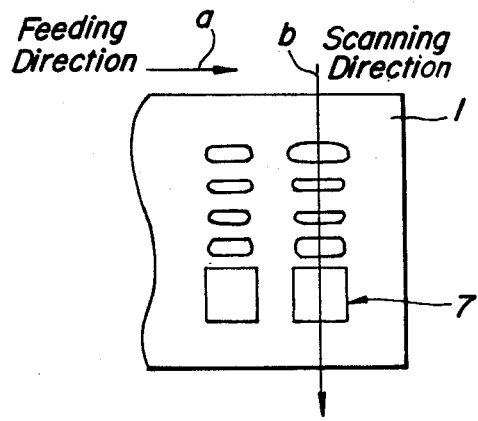
FIG. 2 is a schematic plan view showing a manner of photoelectrically scanning a substrate wearing electrophoretic images.
Figure 3:
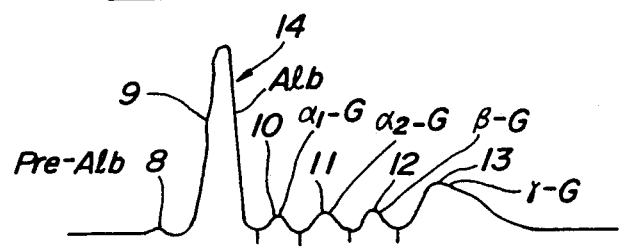
FIG. 3 is a schematic diagram illustrating an electrophoretic image pattern recorded on a test report by the known recording method.
Figure 5:
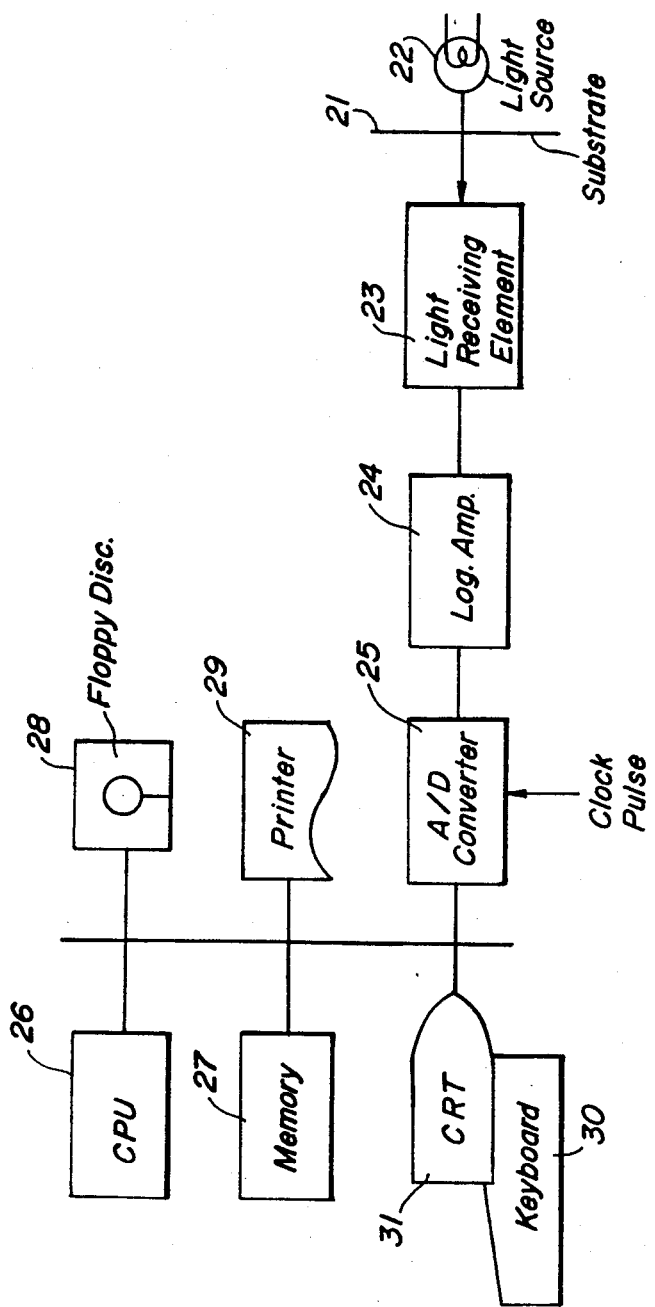
FIG. 5 is a block diagram depicting a general construction of the apparatus for carrying out the method according to the invention.

FIG. 5 is a block diagram illustrating an embodiment of an apparatus for carrying out the recording method according to the invention. In the present embodiment, various kinds of proteins contained in serum samples of human beings are to be analyzed. One or more sets of electrophoretic images of one or more serum samples are formed on a substrate 21 and are photoelectrically scanned by a densitometer comprising a light source 22 and a light receiving element 23. The construction of the densitometer itself is the same as that of the known densitometer shown in FIG. 1. The light source 22 and light receiving element 23 are moved in a scanning direction relative to the substrate 21 at a constant speed, e.g. 8 mm/sec. An output photoelectrically converted signal from the light receiving element 23 is amplified by a log-amplifier 24 and is converted into a signal representing an optical absorbance of electrophoretic images, i.e. fraction images of various kinds of proteins. Therefore, this signal is also called an electrophoretic signal. Then, the converted electrophoretic signal is sampled and converted into digital samples by an A/D converter 25 in synchronism with clock pulses having a repetition period corresponding to a sampling period which may be determined in accordance with analytic conditions such as electrophoretic time period. In the present embodiment, the sampling period is set to 12 m sec, while the electrophoretic time is set to 40 minutes. The digital samples thus obtained are supplied to a memory 27 and are stored therein under the control of a central processing unit (CPU) 26. The apparatus further comprises a keyboard 30 and a cathod ray tube (CRT) 31 for entering and monitoring various commands, data and images.

In the present embodiment, the photometered samples stored in the memory 27 are subjected to the smoothing treatment and the auto-zero treatment for removing any fluctuation of a base line due to a variation in an intensity of light. Then, a predetermined feature of the electrophoretic image is extracted to find a reference point in the electrophoretic images. Generally, a peak point of a fraction image of albumin which generally shows the maximum peak may be set as the reference point. Next, a predetermined number of samples among the samples stored in the memory 27 are selected in accordance with the extracted reference point. In this embodiment, a hundred samples including the sample at the reference point are selected on one side of the reference point, i.e. the peak point of the albumin fraction image and two hundreds and fifty samples are selected on the other side of the reference point. In this manner, three hundreds and fifty samples are totally extracted from the samples stored in the memory 27 on the basis of the reference point on the electrophoretic fraction images.

Figure 6:
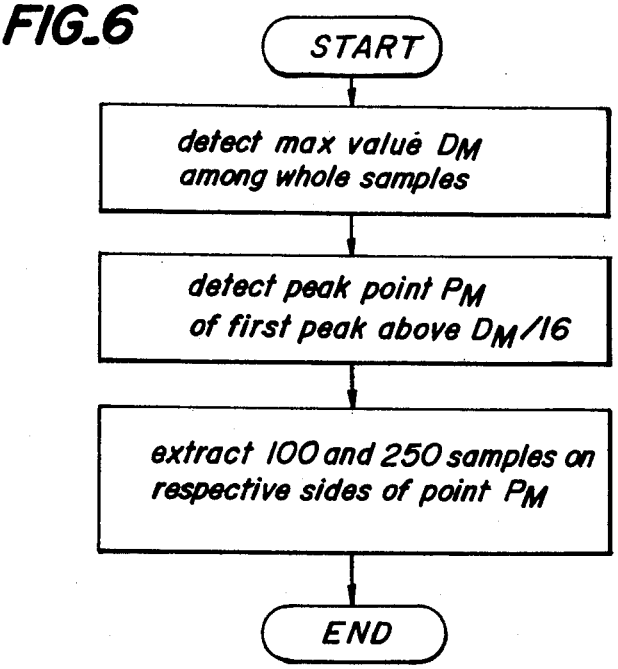
FIG. 6 is a flow chart explaining the operation of an embodiment of the recording method according to the invention.
Figure 7:
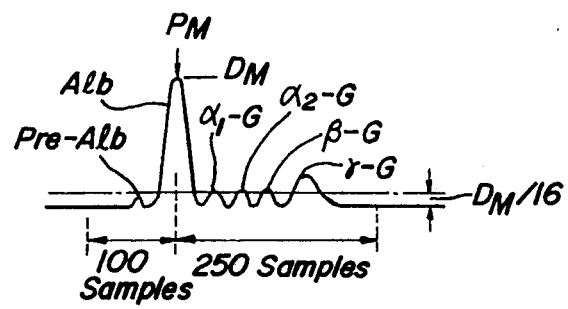
FIG. 7 is a schematic diagram of the electrophoretic image pattern for explaining the recording method according to the invention.
Figure 8:
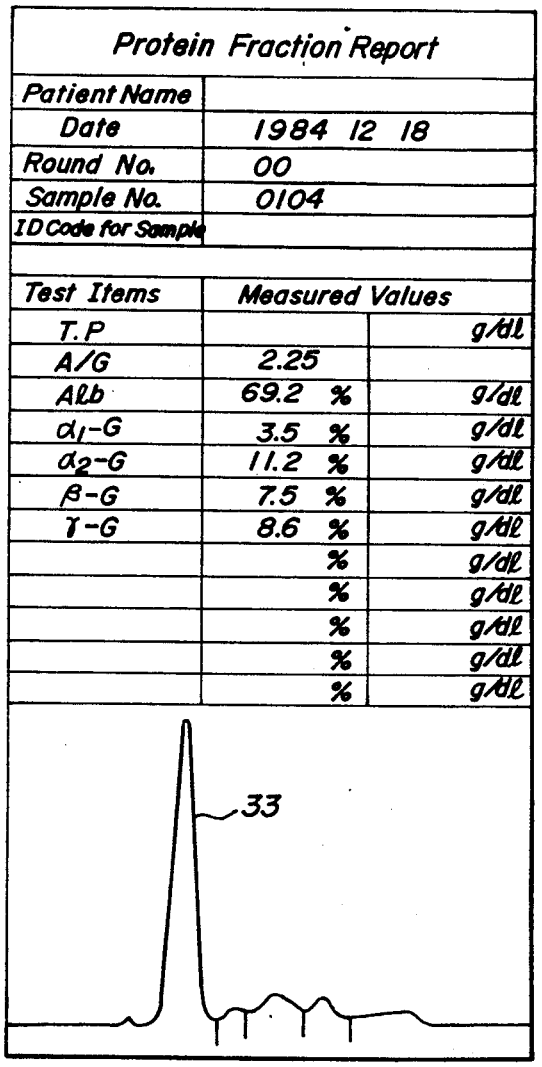
FIG. 8 is a plan view showing a test report on which an electrophoretic image pattern is printed by the method according to the invention.

The extraction of samples may be carried out in various methods, and in the present embodiment, the following method is employed. As illustrated in FIG. 6, first of all a sample having the maximum value $D_M$ is found among all the samples stored in the memory 27. Then, a threshold level having an amplitude corresponding to one sixteenth of the maximum value $D_M$ is derived. Next, as shown in FIG. 7, the samples are successively compared with the threshold value $D_M/16$ from a side of a pre-albumin and a first peak exceeding the threshold level is determined as the peak of the fraction image of albumin Alb and its peak point $P_M$ is detected as the reference point. It should be noted that the threshold value $D_M/16$ has been experimentally determined in such a manner that the peak point $P_M$ of albumin can be always detected as a first peak point under various conditions of sample serums. Therefore, the threshold value is not limited to $D_M/16$, but may be set to any desired value. After the peak point $P_M$ of the fraction image of albumin has been detected as the reference point, a hundred samples on the side of the prealbumin with respect to the reference point $P_M$ and two hundred and fifty samples on the side of the $\gamma$-globulin are extracted from the whole samples stored in the memory 27. Then three hundreds and fifty samples thus extracted on the basis of the peak point $P_M$ of the fraction image of albumin are used to effect the fraction point detecting process and the calculations of fraction percentages and ratio of albumin to globulin (A/G). The measurement results of these processes are stored in a floppy disc 28. After that, in response to commands supplied from CPU 26, the calculated fraction percentages and ratio A/G are printed on give columns of a protein fraction report 32 shown in FIG. 8 by means of a printer 29. Further an electrophoretic image pattern 33 is recorded in a given area of the report 32 by using the extracted 350 samples. Upon recording the electrophoretic image pattern on the report 32, the so-called auto-span is effected such that the maximum value $D_M$ has a predetermined length on the report 32.

According to the invention, since the samples to be used for recording the electrophoretic image pattern are selected on the basis of the reference point on the fraction images, e.g. the peak point of albumin and the electrophoretic image pattern is printed on the report in such a manner that the peak point of albumin fraction image is made coincident with a predetermined position on the report, it is always guaranteed that the electrophoretic image patterns are always recorded at the same position on the reports and thus all the necessary images are recorded without loss, even though the substrate 21 might be fed along an inclined path in the densitometer.

Figure 9:
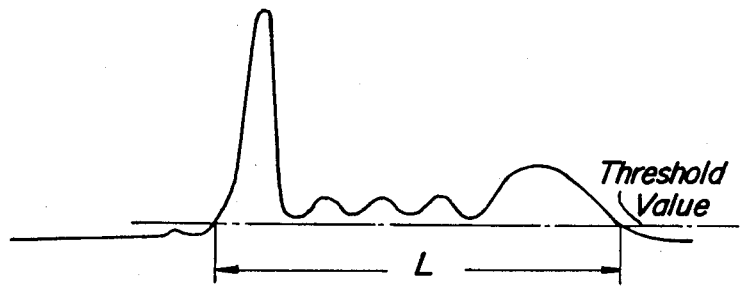
FIG. 9 is a schematic diagram of the electrophoretic image pattern for explaining the operation of another embodiment of the method according to the invention.

According to the further aspect of the invention it is possible to record the electrophoretic image pattern at a correct position on the test report even if the electrophoretic time is varied in accordance with kinds of samples and a process speed. In an embodiment of the method according to the invention, the electrophoretic image formed on the substrate is prescanned and an electrophoretic signal is sampled with a reference sampling period, e.g. 12 m sec. to derive a number of samples. Then, the samples are compared with a predetermined threshold values shown in FIG. 9 to detect an electrophoretic expansion length L within which samples exceed the threshold value. Then the electrophoretic image is photoelectrically scanned again and a photoelectric signal is sampled with a sampling period corresponding to said electrophoretic expansion length L. For instance, the sampling period may be determined in proportion to the electrophoretic expansion length L. A number of samples thus obtained are processed in the same manner as that of the previous embodiment to extract a predetermined number of samples within a given range on the basis of a reference point in the electrophoretic image and then required measurements are effected by using the extracted samples. Finally the measured results and the electrophoretic image pattern are recorded on the report.

The sampling period R in relation to the electrophoretic expansion length L may be determined in accordance with the following equation;

$$R = L/(m \times s)$$

wherein m is the number of samples within the length L and s is the scanning speed for the substrate. In the present embodiment, m is set to 250 and s is 8 mm/sec.

Examples of the sampling period R determined in accordance with the length L are represented in the following table.

| Electrophoretic Period | Electrophoretic Expansion Length L | Sampling Period R |
|---|---|---|
| 40 minutes | 30 mm | 15 m sec |
| 30 minutes | 24 mm | 12 m sec |

In this manner, also in the present embodiment, the electrophoretic image pattern can be always recorded at a correct position on the test report in an accurate and stable manner even if the electrophoretic expansion length L is varied. Further, all of the necessary samples are always recorded on the report sheet and thus the diagnose can be performed in an easy and accurate manner with reference to the measured values and electrophoretic image pattern recorded on the report sheet.

It should be noted that the present invention is not limited to the embodiments explained above, but various alternations and modifications can be conceived by those skilled in the art. For instance, in the above embodiments the reference point is set to the peak point of the fraction image of albumin, but a peak point of a fraction image of any other components, for instance, $\gamma$-globulin or $\alpha_2$-globulin, may be employed as the reference point. Also in such a case, after the maximum value $D_M$ is detected, a peak point of a given fraction image is detected by comparing the successive samples with the threshold level, e.g. $D_M/16$ and counting the number of detected peaks. Moreover, the number of samples to be extracted in accordance with the reference point may be set to any desired value, and the numbers of samples to be extracted from respective sides of the reference point may be suitably selected in accordance with a position of the reference point in the electrophoretic images.

As illustrated in FIG. 4A, on the test report 15, there are generally printed the measured values of fraction percentages and the electrophoretic image pattern in separate areas. Further, standard fraction percentage values denoting normal ranges for respective test items are also printed on the test report. These standard fraction percentage values may be entered into the CPU with the aid of the keyboard and monitor CRT. Principally the morbidity can be derived by inspecting a shape of the electrophoretic image pattern and more precise or detailed analysis for the morbidity can be performed by additionally checking whether the fraction percentages of the various kinds of proteins are within the normal ranges or not. In order to assist this checking, each measured fraction percentages are compared with the respective normal ranges and if a measured fraction percentage is lower or higher than the minimum or maximum value, a character [L] or [H] is respectively printed in a column of a relevant test item on the test report as illustrated in FIG. 4A. This judgement is carried out automatically by the CPU and provides very useful data for doctors. However, in the known test report, such judgement results are printed separately from the electrophoretic image pattern, so that it is rather cumbersome to relate the judgement results and the electrophoretic image pattern with each other. Due to this fact abnormality might be ignored and test items showing abornmality might be mistaken. This might result in serious mis-diagnose.

According to another aspect of the invention, the above disadvantage can be mitigated by simply adding marks denoting abnormality to fraction images whose fraction percentages are out of normal ranges. In this case, it is preferable to form a mark in such a manner that it additionally indicates that a related fraction percentage is lower than or higher than the minimum or maximum value of a normal range.

Now an embodiment of the recording method according to the invention which can record marks indicating the abnormality of fraction percentages of the electrophoretic images in conjunction with the electrophoretic image pattern will be explained with reference to FIGS. 5 and 10. Also in this embodiment, the substrate 21 bearing the electrophoretic images is introduced into the densitometer and the electrophoretic images are photoelectrically scanned by means of the light source 22 and light receiving element 23. The photoelectrically converted signal from the light receiving element 23 is processed by the log-amplifier 24 and A/D converter 25, successively to derive a number of digital samples. The digital samples are stored in the memory 27 under the control of the CPU 26. Then, the samples are processed in the manner explained in the previous embodiments and a predetermined number of samples are extracted on the basis of a reference point in the electrophoretic images.

The various values denoting the normal ranges of total protein (T.P), ratio of albumin to globulin (A/G) and fraction percenages of albumin and various kinds of globulines are previously entered into the floppy disc 28 with the aid of the keyboard 30 and CRT 31. The following table represents as example of such normal values.

| Test Item | Normal Range | | Note |
| --- | --- | --- | --- |
| | L | H | |
| T.P | 3.68 | 8.32 | G/dl |
| A/G | 1.03 | 1.83 | % |
| ALB | 68.5 | 73.5 | % |
| $\alpha_1$-G | 2.3 | 5.2 | % |
| $\alpha_2$-G | 2.1 | 4.8 | % |
| $\beta$-G | 5.7 | 9.2 | % |
| $\gamma$-G | 8.3 | 13.8 | % |

The samples extracted are processed to detect separation points between the fraction images and then fraction percentages and A/G are calculated.

Figure 10:
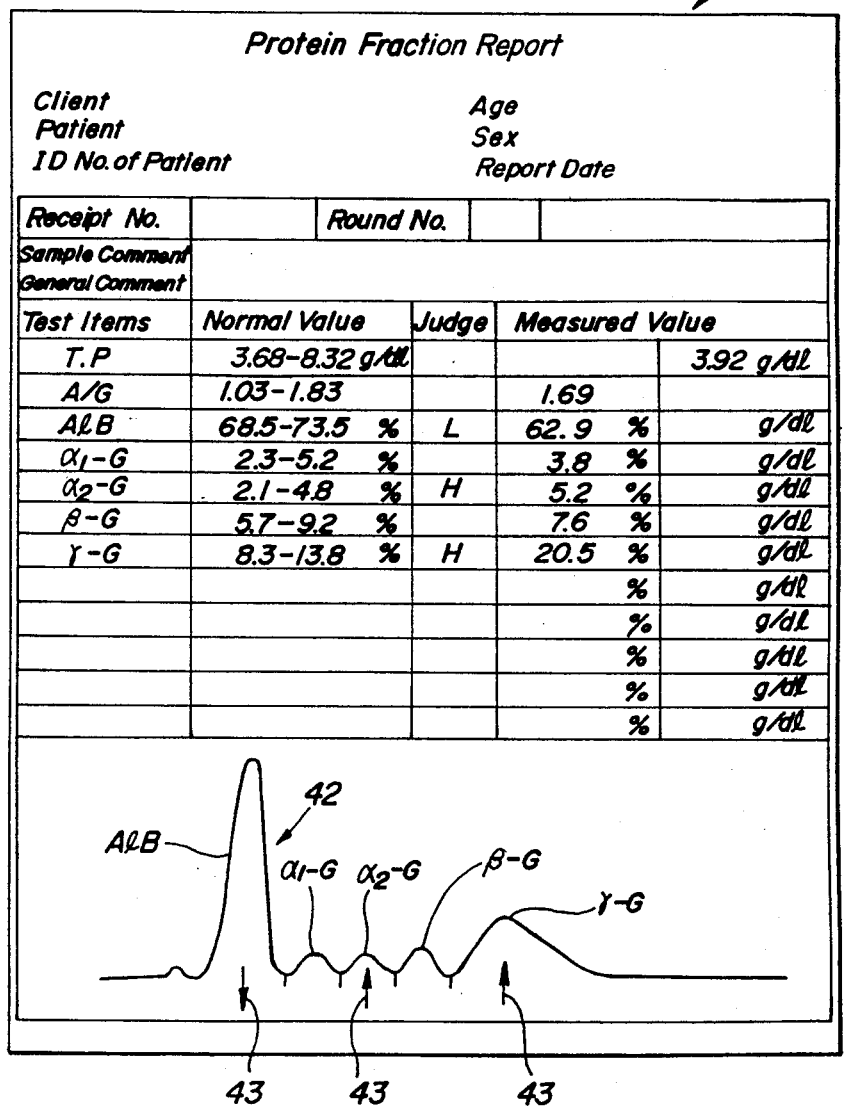
FIG. 10 is a plan view showing a test report having an electrophoretic image pattern printed thereon by another embodiment of the method according to the invention.

The various measurement results thus calculated are printed in given columns on a test report 41 as shown in FIG. 10 by means of the printer 29. On the test report 41 there are further printed the normal values and the judgement results. As explained above, the judgement results are denoted by characters [L] and [H]. Further, an electrophoretic image pattern 42 is printed on the report 41 in the auto-span mode such that the peak value of fraction image of albumin has a predetermined maximum height. According to this embodiment, there are further printed arrow marks 43, " ↑ " and " ↓ " indicating the abnormality. That is to say, when a measured value of a substance is lower than the minimum value of a normal range, the mark " ↓ " is printed at a fraction image of the relevant component, and a measured value is higher than the maximum value of a normal range of a component, the mark " ↑ " is formed at a fraction image of the relevant component. In the present example the mark " ↓ " aheading downward is printed at the fraction image of albumin (Alb) and the marks " ↑ " directing upward are printed at the fraction images of $\alpha_2$-globulin ($\alpha_2$-G) and $\gamma$-globulin ($\gamma$-G). Therefore, a doctor can recognize what components are out of the normal ranges in which direction, i.e. higher or lower in an accurate and simple manner only by inspecting the area of the test report 41 including the electrophoretic image pattern. Therefore, a possibility of ignoring the abnormality and of confusing components showing the abnormality can be effectively decreased, and any mis-diagnose can be efficiently avoided.

In alternative embodiments, the values representing the normal ranges may be recorded as values in g/dl by multiplying the fraction percentages by the total protein amount (T.P). Further, if one or more test items are not analyzed, normal ranges related thereto may be set to 0.0—0.0. Then the print of undesired marks may be avoided. Moreover, positions of the abnormal marks may be selected at any positions with respect to the electrophoretic image pattern 42. For instance, the marks 43 may be printed above the electrophoretic image pattern 41 near related peak points as illustrated in FIG. 11A. In FIG. 11B, the mark " ↓ " which indicates that a fraction percentage is lower than the minimum value is printed above the pattern 41 at a related peak point and the mark " ↑ " representing that a fraction percentage is higher than the maximum value is formed below the pattern at a related peak point. Further, the mark " ↓ " may be provided below the pattern at a related peak point and the mark " ↑ " may be printed above the pattern at a peak point as depicted in FIG. 11C. Moreover, black triangular marks " ▲ " and " ▼ " directing opposite directions may be used as the abnormal mark as illustrated in FIG. 11D. In all the above explained embodiments, there are used the abnormal marks having the indication for denoting the direction in which a related value is out of the normal range, but according to the invention it is also possible to use marks which merely represent the abnormality. FIG. 11E illustrates an embodiment of such abnormal marks 44 in which fraction images showing the abnormality are provided with cross hatchings.

As explained above, the electrophoretic image pattern is printed on the test report with the aid of the printer 29 shown in FIG. 5. To this end, the operation of the printer is controlled by the CPU 26. Usually, the auto-span control is effected such that a height of the fraction image of albumin (Alb) is made equal to a predetermined maximum height. Therefore, it is impossible to change the size of the electrophoretic image pattern at will. As explained above, the morbidity can be diagnosed by inspecting the shape of the electrophoretic image. However, since the size of the electrophoretic image pattern could not be changed at will, it is rather difficult or at least inconvenient to diagnose the morbidity from the shape of the electrophoretic image pattern. For instance, if an amount of albumin contained in a sample serum is excessively large, the fraction images of remaining globulins will be made very small and therefore the shape of these fraction images could not be inspected precisely and the diagnosis could not be performly accurately.

In a further aspect of the method according to the invention the above drawback can be avoided by providing a printer control method for changing at will a size of the electrophoretic image pattern to be recorded on the test report. An embodiment of the recording method according to the invention which performs the above function will be explained hereinbelow.

Also in this embodiment, the photoelectric signal obtained by scanning the substrate bearing the electrophoretic images is processed in the same manner as described in the previous embodiments to derive a predetermined number of digital samples. Then the fraction points between the fraction images are detected and the fraction percentages of albumin, $\alpha_1$-globulin, $\alpha_2$-globulin, $\beta$-globulin and $\gamma$-globulin and a ratio of albumin to globulin (A/G) are calculated and are stored in the floppy disc 28. In order to record the electrophoretic image pattern on a test report, the samples are subjected to the auto-span process to obtain normalized samples in such a manner that the maximum value is converted into a predetermined value of, for example twelve bits. These normalized samples are also stored in the floppy disc 28.

In the present embodiment, in order to print the measured values stored in the floppy disc 28 in given columns on the test report and to print at least a part of an electrophoretic image pattern which will be formed by the normalized samples on the test report at enlarged or reduced scale, necessary display commands are entered and are stored in the floppy disc 28 with the aid of the keyboard 30 and CRT 31. As the printer 29 use may be made of image printer or graphic printer. In the present embodiment, the printer 29 is formed by an eight-bit thermal printer of friction feed mode illustrated in FIG. 12, and use is made of the protein fraction report 51 having a top of form (TOF) mark 52 as shown in FIG. 13.

Figure 12:
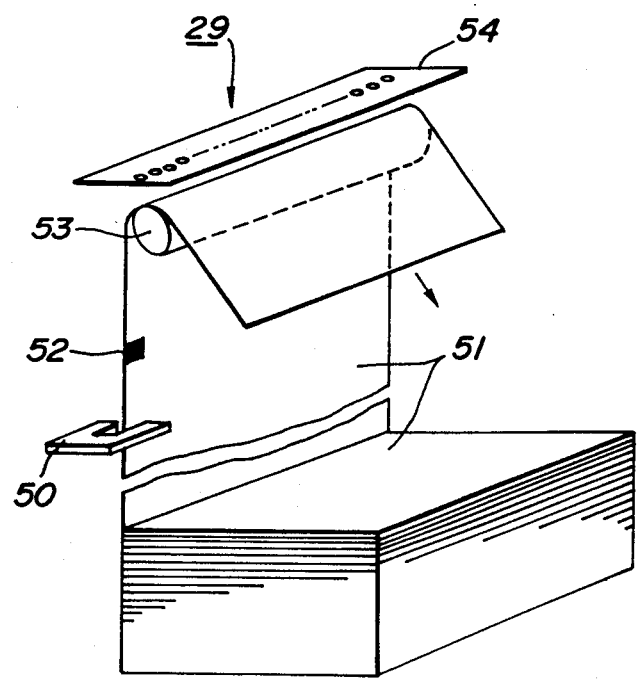
FIG. 12 is a schematic perspective view illustrating an embodiment of a printer.
Figure 13:
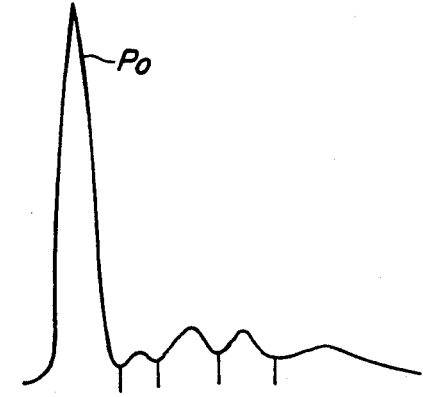
FIG. 13 is a plan view of a test report on which an electrophoretic image pattern is printed by still another embodiment of the recording method according to the invention.

In FIG. 12, the printer 29 comprises a sensor 50 for detecting the TOF mark 52 on the report 51, a paper feed roller 53 and a heater head 54 including a heater dot array having a density of 6 dots/mm. By controlling the printer dots in ON-OFF manner, desired data and pattern can be printed in a predetermined area 51a on the test report 51. The printer 29 is controlled by the CPU 26 to initiate the paper feeding in response to the entrance of the TOF code, and after that the paper feeding is temporarily stopped in response to a signal which is generated when the sensor 50 detects the TOF mark 52. At this moment, the heater head 54 faces against the first column of the test report 51. Thereafter the operation of printing the measured values in given columns on the test report 51 and the operation of feeding the test report with respect to the heater head 54 are controlled by the CPU 26. However, the position of the report 51 relative to the heater head 54 is varied due to the variation in the relative position of the sensor 50 and heater head 54, any possible deviation in position of the TOF mark 52 and columns printed on the report 51, and the exchange of the report 51. Due to this variation in position the measured value might not be recorded in given columns correctly. In order to compensate such variation, TOF correction data is entered as a display instruction and is stored in the floppy disc 28.

An example of the display commonds for controlling the printer 29 will be shown in the following table.

| Print Item | Print Line, Digit |
| --- | --- |
| T.P | 8, 3 |
| A/G | 9, 5 |
| ALB | 10, 3 |
| $\alpha_1$-G | 11, 3 |

-continued

| Print Item | Print Line, Digit |
| --- | --- |
| $\alpha_2$-G | 12, 3 |
| $\beta$-G | 13, 3 |
| $\gamma$-G | 14, 3 |
| Patient Name | 1, 1 |
| Date | 2, 1 |
| Round No. | 3, 1 |
| Sample No. | 4, 1 |
| Sample ID No. | 5, 1 |
| Comment | 6, 1 |
| Phoretic Pattern | 20, 10 |
| Magnification | 10/83 |
| TOF Correction | 5 |

Figure 14:
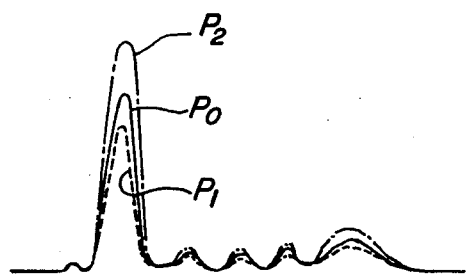
FIG. 14 shows three electrophoretic image patterns having different magnifications.

In the above table, the number "5" of the TOF correction indicates that after the TOF operation, the test report 51 should be fed by five dots to adjust the relative deviation in position between the report 51 and the heater head 54. Then, the measured values are printed in given columns correctly. Further, the number "10/83" of the magnification represents a standard longitudinal magnification of the electrophoretic image pattern to be printed on the test report 51. That is to say, when the magnification command is set to "10/83", an electrophoretic image pattern $P_0$ having a standard magnification or size is printed on a pattern print area 51a of the test report 51 as illustrated in FIG. 13. If the magnification command is set to a value samller or larger than 10/83, it is possible to print an electrophoretic image patterns $P_1$ or $P_2$ having smaller or larger size as shown in FIG. 14.

Figure 15:
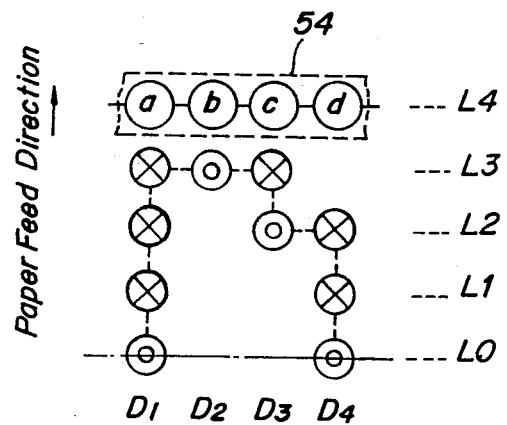
FIG. 15 is a schematic view showing the operation of the printer.

Next, a process for recording the electrophoretic image pattern on the report will be explained. At first the normalized samples stored in the floppy disc 28 are read out and are stored in the memory 27. Then the normalized samples are multiplied with the magnification entered as the magnification command. It is now assumed that four multiplied samples D1 to D4 are 0, 3, 2 and 0, respectively. In this case, if the heater head 54 records only dots denoted by ⊙ in FIG. 16 which illustrates a dot pattern on the report 51, a continuous electrophoretic image pattern could not be recorded. In order to form the electrophoretic image written by a continuous line, in the present embodiment an interpolation is employed such that dots denoted by (X) are also recorded. The interpolation itself has been well known in the art and thus is not explained here further in detail. After the interpolation has been completed and necessary data has been stored in the memory 27, the test report 51 is fed dot by dot and at the same time dots a to d of the heater head 54 of the printer 29 are controlled in accordance with the dot data read out of the memory 27 under the control of the CPU 26. In the example shown in FIG. 15, when the heater head 54 is positioned at a line L4, all the dots a to d are remained inoperative. At a next line L3, dots a, b and c are energized simultaneously, and at a line L2 dots a, c and d are driven. At a next line L1, dots a and d are made operative, and at a base line L0 dots a and d are energized. In this manner, the continuous electrophoretic image pattern is printed As explained above, in the present embodiment it is possible to record the electrophoretic image pattern having a desired magnification or size and the maximum resolution of the printer 29 can be utilized by multiplying the normalized samples stored in the floppy disc 28 by the entered magnification command and by effecting the interpolation.

FIG. 16 is a flow chart showing the successive steps of the recording method of the present embodiment. Since the contents of the flow chart have been explained, a detailed explanation thereof may be dispensed with.

In the above embodiment, the size or magnification of the electrophoretic image pattern is made adjustable only in the vertical direction, however, according to the invention one or both of vertical magnification and horizontal magnification may be adjusted. Moreover, according to the invention, only a part of the electrophoretic image pattern may be selectively printed on the test report as shown in FIG. 17A. In this case, the size or magnification of the part of the pattern to be displayed may set at will. Further, as illustrated in FIG. 17B, a part of the electrophoretic image pattern may be printed with a magnification different from the remaining part of the pattern. Furthermore, the electrophoretic image pattern $P_0$ having the standard magnification and an additional pattern $P_A$ of a part of the pattern $P_0$ having an enlarged or reduced scale may be simultaneously printed as shown in FIG. 17C. In case of printing the patterns shown in FIGS. 17A to 17C it is preferable to display an image of the electrophoretic image pattern having the standard magnification on the CRT 31. Then display commands for indicating the position and magnification of the pattern to be printed may be entered with the aid of the keyboard 30.

It should be noted that the present invention is not limited to the embodiments mentioned above, but many modifications and alternations may be conceived by those skilled in the art within the scope of the invention. For instance, in the above embodiments, the electrophoretic image pattern is recorded by printing the pattern on the test report by means of the printer. However, the electrophoretic image pattern may be recorded by displaying the pattern on the monitor screen. In such a case, the printer may be dispensed with.

As explained above, in the present embodiment, since at least a part of the electrophoretic image pattern can be printed at a desired magnification, the inspection of the pattern in relation to the morbidity can be performed easily and precisely and therefore, the correct diagnose can be provided and a possibility of misdiagnose can be effectively reduced.

What is claimed is:

1. A method of recording an electrophoretic image pattern of components contained in a sample by printing or displaying the pattern on a test report or a monitor screen comprising the steps of:
   (a) processing an electrophoretic image signal obtained by photoelectrically scanning electrophoretic images formed on a substrate to detect a predetermined reference point in the electrophoretic images;
   (b) extracting a given portion of the electrophoretic image signal on the basis of the detected reference point; and
   (c) recording an electrophoretic image pattern in accordance with the extracted portion of the electrophoretic image signal.

2. A method according to claim 1, wherein said step (a) comprises
   (a-1) sampling the electrophoretic signal with a sampling period to derive a number of samples,
   (a-2) detecting the maximum amplitude of all the samples, and
   (a-3) determining a position of a reference sample in relation to said maximum amplitude as said reference point in the electrophoretic images; said step (b) comprises
   (b-1) extracting a predetermined number of samples in accordance with said reference sample; and said step (c) comprises
   (c-1) recording the electrophoretic image pattern by using the predetermined number of samples thus extracted.

3. A method according to claim 2, wherein said steps (a-3) of determining the position of the reference sample comprises
   comparing all the samples with a predetermined fraction of the maximum amplitude to detect a plurality of peaks; and
   determining a sample showing a predetermined peak as the reference sample.

4. A method according to claim 3, wherein said predetermined fraction of the maximum value is so determined that it exceeds a peak value of a pre-albumin.

5. A method according to claim 2, wherein said sampling period is fixed to a predetermined period.

6. A method according to claim 5, wherein said sampling period is determined in accordance with an electrophoretic time.

7. A method according to claim 2, wherein said sampling period is made variable in accordance with an electrophoretic time period.

8. A method according to claim 7, wherein the electrophoretic signal is sampled with a first fixed sampling period to derive a first set of samples, the first set of samples are compared with a threshold level to detect an electrophoretic expansion length (L), the electrophoretic signal is sampled again with a second sampling period which is determined in accordance with the electrophoretic expansion length, to derive a second set of samples.

9. A method according to claim 8, wherein said second sampling period (R) is determined in accordance with an equation, $$R = L/(m \times s)$$

wherein m is the number of samples within the electrophoretic expansion length and s is a speed of photoelectrically scanning the electrophoretic images formed on the substrate.

10. A method according to claim 1, further comprising the steps of:
    (d) calculating analyzed amounts of the components contained in the sample;
    (e) comparing the analyzed amounts with normal ranges of the components; and
    (f) printing an abnormal mark on the test report in the vicinity of the electrophoretic image pattern, when an analyzed amount of a component is out of a normal range of the relevant component.

11. A method according to claim 10, wherein said calcuating step (d) comprises fthe step of:
    (d-1) determining fraction points of fraction images of the electrophoretic image pattern, and
    (d-2) calculating fraction percentages of the fraction images as the analyzed amounts.

12. A method according to claim 11, further comprising the step of (d-3) calculating fraction concentration values (g/dl) from the fraction percentages and an amount of total protein (T.P) which is measured separately.

13. A method according to claim 10, wherein an analyzed amount is compared with maximum and minimum values denoting a normal range, and said abnormal mark has such a shape that the abnormal mark indicates whether the analyzed amount is higher than the maximum value or lower than the minimum value.

14. A method according to claim 12, wherein said abnormal mark is formed as a single-headed arrow.

15. A method according to claim 12, wherein said abnormal mark is formed by a triangle.

16. A method according to claim 10, wherein said abnormal mark is printed or displayed in the vicinity of a peak point of a relevant electrophoretic image.

17. A method according to claim 1, wherein said electrophoretic image pattern is printed or displayed on the test report or the monitor screen in such a manner that at least a part of the electrophoretic image pattern is printed or displayed with an enlarged or reduced magnification with respect to a standard magnification.

18. A method according to claim 17, wherein said standard magnification is determined such that a sample having a maximum amplitude is so printed or displayed on the test report or the monitor screen that the sample has a predetermined maximum length.

19. A method according to claim 18, wherein the samples are normalized with respect to said maximum amplitude to derive normalized samples, and at least a part of the normalized samples are multiplied with a desired magnification.

20. A method according to claim 17, wherein only a part of the electrophoretic image pattern is printed or displayed on the test report or the monitor screen.

21. A method according to claim 17, wherein the electrophoretic image pattern having the standard magnification and a part of the electrophoretic image pattern having an enlarged or reduced magnification are printed or displayed on the test report or the monitor screen side by side.

22. A method according to claim 17, wherein said enlarged or reduced magnification is entered with the aid of a keyboard.

* * * * *